(12) United States Patent
Schulze

(10) Patent No.: US 6,712,829 B2
(45) Date of Patent: Mar. 30, 2004

(54) VESSEL EVERSION INSTRUMENT WITH CONICAL, EXPANDABLE MANDREL

(75) Inventor: Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/949,739

(22) Filed: Sep. 10, 2001

(65) Prior Publication Data

US 2003/0050652 A1 Mar. 13, 2003

(51) Int. Cl.[7] .............................................. A61B 17/04
(52) U.S. Cl. ....................................... 606/149; 606/198
(58) Field of Search ........................ 606/149; 604/107, 604/106

(56) References Cited

U.S. PATENT DOCUMENTS

| | | | | |
|---|---|---|---|---|
| 668,879 | A | * | 2/1901 | Miller ......................... 27/21.1 |
| 2,086,371 | A | | 7/1937 | Tear |
| 2,940,452 | A | | 6/1960 | Smialowski |
| 3,040,748 | A | | 6/1962 | Klein et al. |
| 3,057,355 | A | | 10/1962 | Smialowski et al. |
| 3,180,337 | A | | 4/1965 | Smialowski |
| 3,908,662 | A | | 9/1975 | Razgulov et al. |
| 4,470,415 | A | | 9/1984 | Wozniak |
| 4,622,970 | A | | 11/1986 | Wozniak |
| 4,899,729 | A | * | 2/1990 | Gill et al. .................... 606/198 |
| 5,123,905 | A | * | 6/1992 | Kelman ....................... 606/107 |
| 5,139,511 | A | * | 8/1992 | Gill et al. .................... 606/198 |
| 5,904,699 | A | * | 5/1999 | Schwemberger et al. ... 606/185 |
| 6,027,518 | A | * | 2/2000 | Gaber .......................... 606/198 |
| 6,152,899 | A | * | 11/2000 | Farley et al. ................ 604/113 |
| 6,402,764 | B1 | * | 6/2002 | Hendricksen et al. ....... 606/149 |
| 2003/0004524 | A1 | * | 1/2003 | Schulze et al. ............. 606/149 |
| 2003/0050651 | A1 | * | 3/2003 | Knight et al. ............... 606/149 |

* cited by examiner

*Primary Examiner*—Michael J. Milano
*Assistant Examiner*—Bradford C Pantuck

(57) ABSTRACT

An instrument for exerting an end of a vessel over an end of a tubular workpiece. The instrument has a body having an axial bore, and a mandrel mounted within the axial bore and partially extending from the distal end of the axial bore. The mandrel is made from a sheet of spring-like material rolled into a conical shape. The distal end of the mandrel is insertable into the lumen of the vessel. A plunger substantially contained within the axial bore and axially moveable, extends into the proximal end of the mandrel and presses against an inner surface of the mandrel when the plunger is moved from a retracted position to an extended position, thereby causing the distal end of the mandrel to expand radially and the proximal end of the mandrel to contract radially. An optional spring mounted to the body provides a biasing force to move the plunger to the retracted position and to allow the mandrel to return to the conical shape.

20 Claims, 2 Drawing Sheets

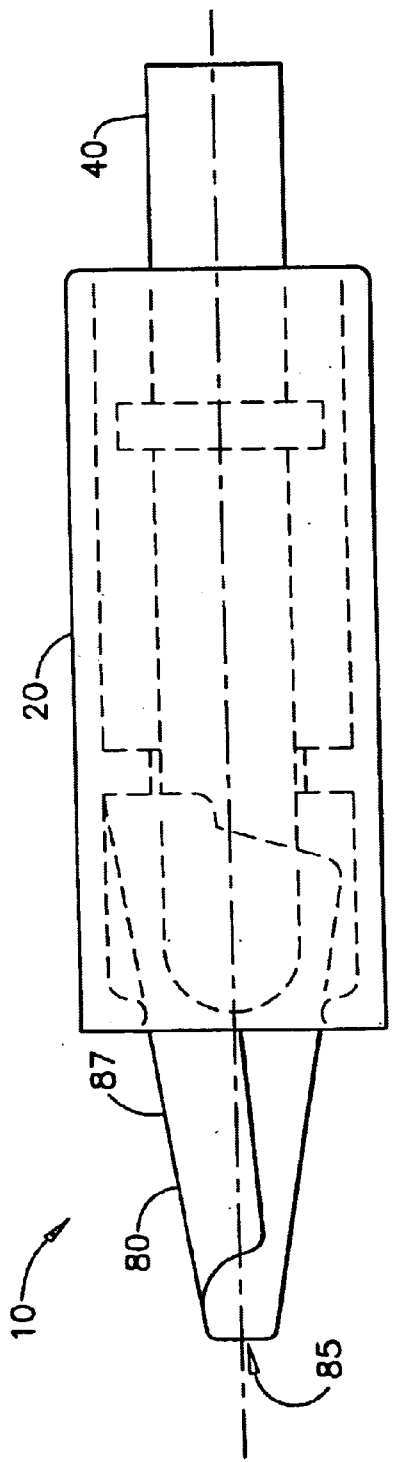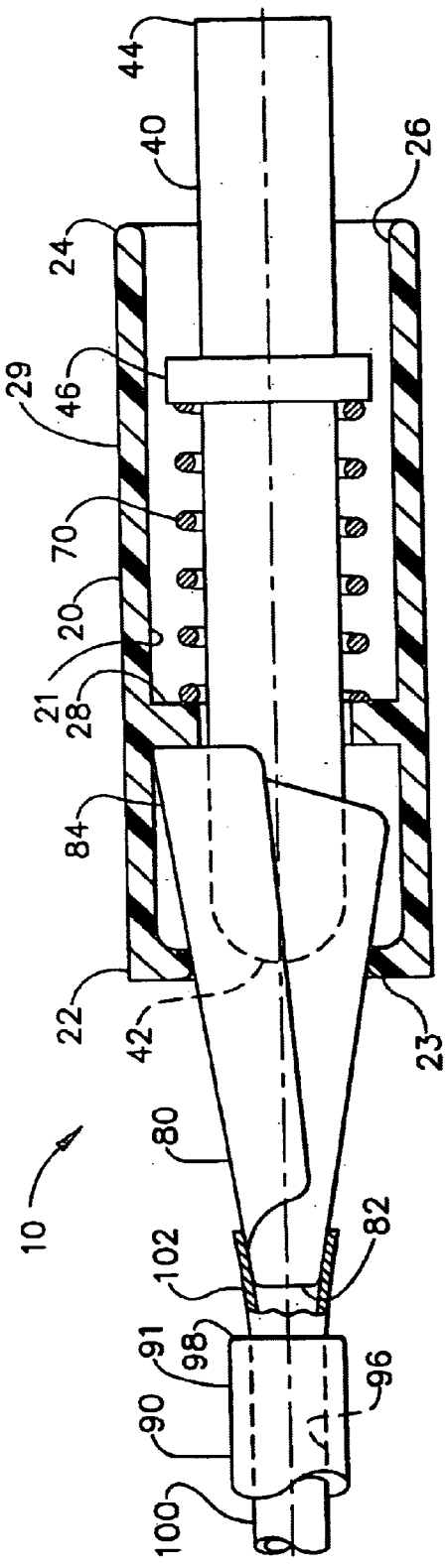

VESSEL EVERSION INSTRUMENT WITH CONICAL, EXPANDABLE MANDREL

FIELD OF THE INVENTION

The field of art to which this invention relates is medical devices, more specifically, medical devices and surgical procedures for performing anastomosis of hollow organs such as blood vessels.

BACKGROUND OF THE INVENTION

Anastomosis surgical procedures are common in the field of cardiac surgery.

These procedures are conventionally used for repairing a damaged or diseased blood vessel. In a typical anastomosis procedure, a surgeon joins a first blood vessel to a second blood vessel and creates a passageway between the two blood vessels to provide for the communication of blood flow. For this kind of anastomosis, the surgeon typically uses specialized grasping tools to manipulate a tiny, curved needle attached to an extremely fine surgical filament (under 0.001 inch diameter) to suture the vessels together. The vessels may be joined end-to-end, end-to-side, or side-to-side. To facilitate healing of the joined vessels, the prevailing standard of care requires that the surgeon suture the inside surfaces of the first and second vessels together, intima to intima. The surgeon must take great care not to damage the intima of each vessel so that endothelial cells may form over the anastomosis without the formation of thrombus or other complications, thus improving the likelihood of a long term patency of the vessels. For life-saving procedures such as coronary artery bypass graft surgery (CABG), this is especially important. When performing a distal anastomosis in a conventional CABG procedure, the surgeon typically sutures an end-to-side anastomosis of a distal end of a graft vessel (such as a segment of saphenous vein harvested from the patient) to a side of a target vessel (the stenosed coronary artery). For a proximal anastomosis in a conventional CABG procedure, the surgeon sutures a proximal end of the graft vessel to the side of the aorta.

As this field of art has progressed over the last several years, new anastomotic methods have been developed and introduced in attempts to replace the suturing technique briefly described above. Many of these methods incorporate novel fasteners and fastener appliers. The requirement, however, to maintain intima-to-intima contact of the joined vessels remains just as important with these approaches. In fact it is often necessary, prior to joining the vessels, for the surgeon to evert (i.e., turn inside out) the end of at least one of the vessels over the end of a member such as a tube, ferrule, or bushing, etc., which is a component of the fastener or fastener applier. This exposes the intima of that vessel for presentation to the intima of the other vessel prior to fastening the vessels.

Although it is possible to evert larger vessels (over 5 mm in diameter) using standard forceps and graspers available in the operating room, such methods are slow and may result in excessive damage to the vessel everted. And, often the surgeon requires assistance in performing the eversion procedure. Furthermore, vessels smaller than 5 mm are very difficult, if not impossible, to evert using such methods.

There are several requirements for an effective vessel eversion device. As noted earlier, for proper healing, it is important not to injure the intima of either vessel during the eversion procedure. The eversion device also must be easy for the surgeon to use without assistance and require only a few steps to operate. The eversion device must be useful for a wide range of blood vessel sizes, particularly small vessels, e.g., having a diameter of about 2–3 mm or less. In addition, it is desirable for the eversion device to be useful on one end of a vessel, when the opposite end is already attached to the patient (e.g., at the distal anastomosis of a patient undergoing a CABG procedure). The eversion device should also allow for the proper length of everted tissue, depending on the requirements of the anastomosis device or method to be used. Finally, it is desirable that the eversion device is low cost and yet operates reliably.

Accordingly, there is a need in this art for novel devices and methods for engaging and everting the end of a blood vessel (or other tubular body organ), which can be used in a quick and effective manner without causing trauma to the vessel or the intima of the vessel (or tubular body organ).

SUMMARY OF THE INVENTION

It is an object of the present invention to provide novel eversion devices which are easy for the surgeon to use without assistance, and which efficiently and effectively engage blood vessels and evert the ends of blood vessels, including blood vessels having small or fine diameters.

A further object of the present invention is to provide novel eversion devices which engage blood vessels and evert the ends of blood vessels without causing trauma to the blood vessel or the intima of the blood vessels.

It is yet another object of the present invention to provide novel methods of engaging and everting blood vessels quickly and efficiently, while preventing or minimizing damage to the blood vessels and the intimas of the blood vessels.

It is still yet a further object of the present invention to provide a novel vessel eversion device and procedure for everting one end of a vessel having the other end already attached to another vessel.

Accordingly, an eversion instrument for everting an end of a vessel is disclosed.

The instrument has a hollow frame having a distal end, a proximal end, and an axial bore. The axial bore has a distal section and a proximal section. A mandrel member is mounted within the distal section of the axial bore. The mandrel has a proximal end and a distal end, the distal end partially extending from the distal end of the hollow frame. The mandrel member is made from a sheet of spring-like material rolled into a substantially conical shape, having a proximal end, a distal end, an inner surface, and an inner lumen, wherein the distal end of said mandrel is insertable into the lumen of a vessel. And, a plunger member is slidably mounted in the axial bore and axially moveable therein. The plunger member has a distal end and a proximal end. The plunger is moveable in the lumen of the mandrel member, and the distal end of the plunger member engages the inner surface of the mandrel member when the plunger is manually moved from a retracted position to an extended position, thereby causing the distal end of the mandrel member to expand radially outward and the proximal end of the mandrel to contract radially inward.

Another aspect of the present invention is the combination of the above-described instrument and a tubular member. The tubular member has a tubular frame with a distal end, a proximal end, an inner lumen and an outer surface and an inner surface.

Still yet another aspect of the present invention is a method of everting the end of a vessel using the above-described instrument.

These and other aspects and advantages of the present invention will become more apparent from the following description and accompanying drawings.

BRIEF DESCRIPTION OF THE DRAWINGS

FIG. 1 is a side view an eversion instrument 10 of the present invention.

FIG. 2 is a cross-sectional view of eversion instrument 10 of FIG. 1, illustrating a step of inserting eversion instrument 10 into a vessel portion 102.

DETAILED DESCRIPTION OF THE INVENTION

Figure 3:
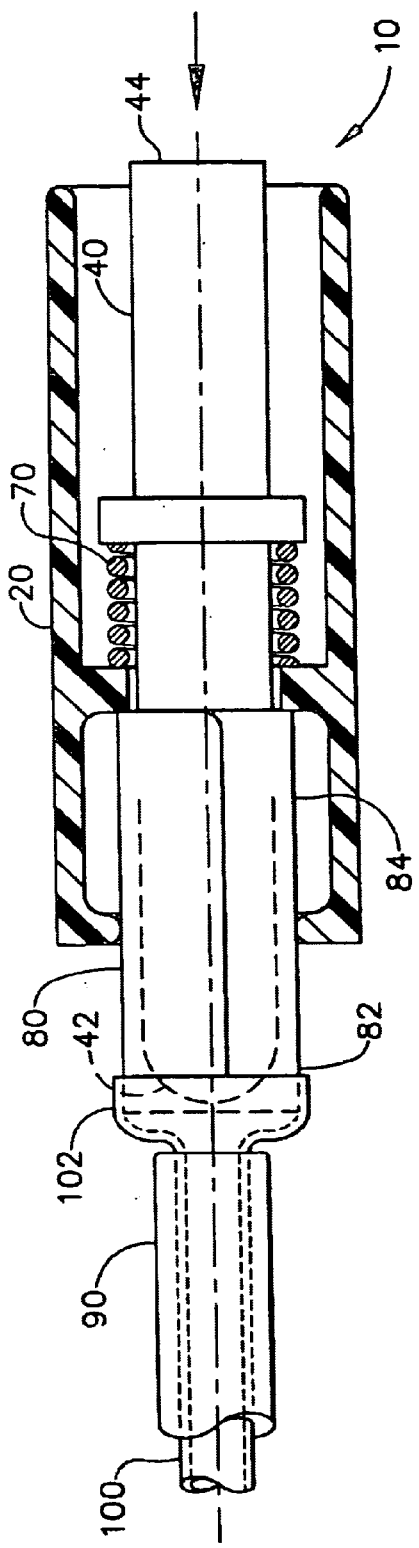
FIG. 3 is a cross-sectional view of eversion instrument 10, illustrating a step of radially expanding vessel portion 102.

An eversion instrument 10 of the present invention useful for everting a vessel portion 102 (see FIG. 2) of a vessel 100 over the distal end of a tube 90, also referred to as a tubular workpiece 90 or a tubular member 90. Vessel 100 may be a blood vessel, such as a segment of the greater saphenous vein, having a diameter of about 2–8 mm, although other hollow organs may be everted using eversion instrument 10. Tube 90 contains or holds vessel 100 and is representative of numerous kinds of bushings, ferrules, tubes, and specialized devices having an approximately cylindrical shape with an axial bore through it. The tube 90 is also seen to have an outer surface 91. Vessel 100 is inserted into an axial bore 92 of tube so that distal vessel portion 102 of vessel 100 extends beyond a distal tube end 98 of tube 90. The length of vessel portion 102 extending out from axial bore 92 beyond distal tube end 98 is sufficient to effectively provide for the desired length of eversion, and is preferably in the range of 5–15 mm. An operator of eversion instrument 10, an assistant, or a mechanical holding device holds tube 90 as the operator uses eversion instrument 10 to evert vessel portion 102 onto the section of tube surface 91 of distal end 98 of tube 90.

As seen in FIGS. 1 and 2, eversion instrument 10 comprises a cylindrical frame member 20 having a distal end 22, a proximal end 24, an inner surface 21 surrounding an axial bore 26 therethrough, and an outer surface 29. If desired frame member 20 may have other geometric cross-sections including oval, square, triangular, rectangular, polygonal, combinations thereof and the like. Eversion instrument 10 further comprises a piston 40 slideably mounted in axial bore 26 of cylinder 20. Piston 40 has a rounded, distal end 42, a proximal end 44, and a ring 46 located approximately halfway between distal end 42 and proximal end 44. A spring 70, preferably a stainless steel, coiled wire, compression spring or equivalent biasing member, mounts loosely over piston 40 and between ring 46 and an internal flange 28 that extends radially inward from inner surface 21 of cylinder 20, thus providing a biasing force to piston 40 in the proximal (right) direction.

Eversion instrument 10 also has a conical element 80 having a distal end 82 and a proximal end 84, an inner lumen 85 and an outer surface 87 mounted in the distal section of the axial bore 26. Distal end 82 is seen to extend out from distal end 22 of frame 20. When unconstrained, conical element 80 is normally in a cone-like configuration with distal end 82 having a much smaller diameter (in the range of 1–3 mm) than the diameter of proximal end 84. Conical element 80 may be made, for example, from a sheet of stiff but resilient material such as approximately 0.25 mm thick polycarbonate (PC) sheet, which has been rolled into a funnel shape, heat set for a few seconds at a temperature just high enough to soften the material, and then permitted to cool while still constrained in the funnel shape. Conical element 80 may be made from sheets of any one of a number of polymeric or metallic materials of varying thicknesses, including approximately 0.25 mm thick cellulose acetate propionate (CAP), and approximately 0.10 mm thick stainless steel foil (shimstock). Preferably, however, conical element 80 is made of a transparent material such as PC or CAP so that vessel portion 102 is visible during each step of the operational sequence for using eversion instrument 10.

FIG. 2 depicts a step of the manual operational sequence for everting vessel 100. The operator holds cylinder 20, preferably between the thumb and second finger, while the index finger is positioned on proximal end 44 of piston 40. Distal end 82 of conical element 80, being smaller in diameter than the opening in vessel portion 102, is easily inserted into lumen 105 of the extending distal section 102 of vessel 100. The operator or an assistant may use fingertips or another surgical instrument such as a probe or a forceps, to "milk" or urge vessel portion 102 onto surface 87 of conical element 80.

FIG. 3 depicts eversion instrument 10 being used in a step of the operational sequence of radially expanding vessel portion 102 of vessel 100. The operator pushes on proximal end 44 of piston 40 while holding cylinder 20 approximately stationary relative to tube 90. Distal end 42 of piston 40 advances distally (left) in lumen 85 to cause conical element 80 to change to a substantially cylindrical configuration as shown. Distal end 82 and proximal end 84 of conical element 80 become approximately equal in diameter, and larger than the diameter of tube 90. The inner lumen 105 in the distal section 102 of vessel 100 similarly has a diameter larger than the outside diameter of distal end 98 of tube 90. Spring 70 compresses, thus increasing the biasing force on piston 40 in the proximal (right) direction.

Figure 4:
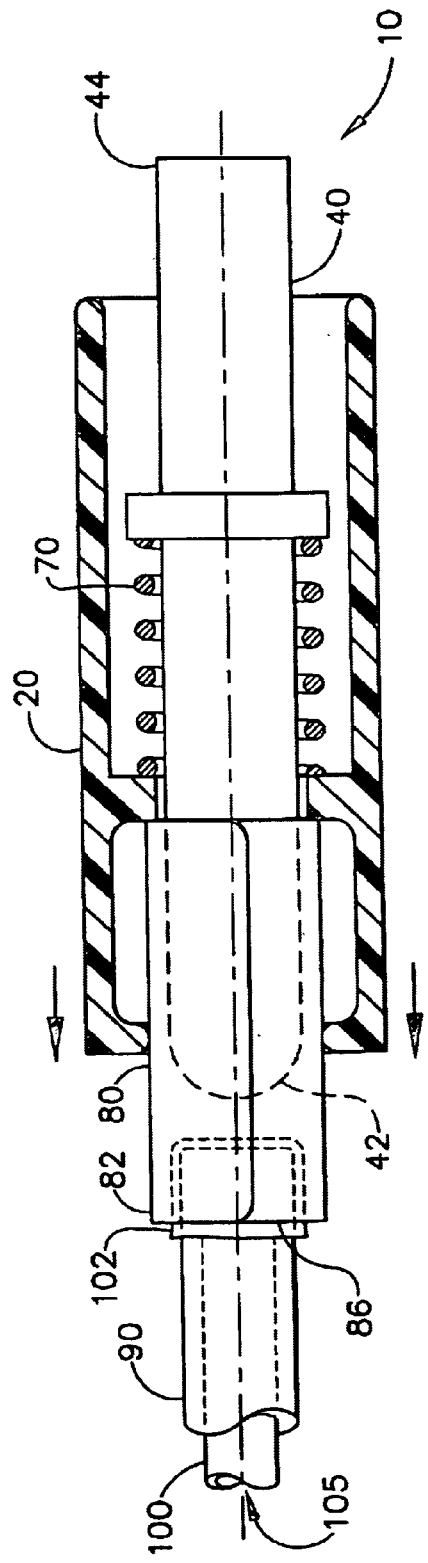
FIG. 4 is a cross-sectional view of eversion instrument 10, illustrating a step of invaginating vessel portion 102.

FIG. 4 depicts eversion instrument 10 being used in a step of the operational sequence of invaginating vessel portion 102 over tube 90 onto surface 91 of distal end 98. The operator moves cylinder 20 in the distal direction (left) so that distal end 82 of conical element 80 passes over tube 90, thus everting vessel portion 102 onto tube 90. The operator releases piston 40, allowing piston 44 to move proximally (to the right) as spring 70 expands and distal end 42 retracts from vessel 100. Eversion instrument 10 may then be slid off of the everted vessel 100 and reset for another use by allowing piston 40 to move further in the proximal direction so that conical element 80 resumes a conical configuration as shown in FIG. 2.

When conical element 80 is in the cylindrical configuration as shown in FIG. 4, a circumferential edge 86 on distal end 82 of conical element 80 is approximately square, that is the imaginary plane defined by circumferential edge 86 is approximately perpendicular to the longitudinal axis of eversion instrument 10. As a consequence, circumferential edge 86 provides a continuous edge for pushing against vessel portion 102 during the step of invaginating. By distributing an everting force circumferentially as in the present invention, less trauma to the vessel occurs than with multi-fingered devices, thus reducing the possibility of injury to the vessel and later complications. Using conical element 80 for the initial flaring or radial stretching of vessel portion 102 also facilitates an even distribution of radial tensile (hoop) stress in the vessel walls, substantially preventing the creation of localized regions of high stress. In addition, vessel portion 102 only needs to be flared or radially expanded to a diameter to fit over tube 90, substantially eliminating overstretching.

Eversion instrument 10 as described for the specific embodiment shown in FIGS. 1–6 is constructed of low cost materials and preferably is supplied to the end user as a sterilized unit intended for single patient use. Re-sterilizable embodiments of eversion instrument 10 intended for multi-patient use will become apparent to those skilled in the art.

The following example is illustrative of the principles and practice of the present invention although not limited thereto.

EXAMPLE

A patient undergoing cardiac coronary artery bypass graft (CABG) surgery is prepared for surgery and anesthetized in a conventional manner in accordance with the prevailing medical standards. The patient's chest is opened in a conventional manner by cutting through the sternum and expanding the rib cage with a conventional surgical retractor instrument. The patient's heart is accessed in a conventional manner and the patient is connected to a pulmonary bypass machine and the heart is stopped. A section of the patient's saphenous vein, which has already been harvested by this time, is prepared for use as a graft vessel. The graft vessel end that is to be attached to the aorta for the proximal anastomosis is everted using an eversion instrument of the present invention as already described in the detailed description and shown in FIGS. 2–4. In FIG. 4, an end 102 of vessel 100 is shown everted over distal end 98 of tube 90. One embodiment of tube 90 is disclosed in published patent application WO0056228, "Low Profile Anastomosis Connector", filed on Mar. 20, 2000, assigned to By-Pass, Inc., and which is hereby incorporated herein by reference. As described in WO0056228, a metallic anastomosis connector comprising a plurality of ring segments is used to fasten the graft vessel to another vessel such as the aorta. The distal end of the graft vessel is then anastomotically attached to a coronary artery on the heart using a conventional hand suturing method. Additional bypasses are performed in the same manner or variations, depending on the patient's condition and anatomy. The remainder of the CABG procedure is conducted in a conventional manner and includes the steps of inspecting and repairing the grafts for leaks, checking blood flow, removing the patient from the pulmonary bypass machine, and closing the surgical incision.

The eversion instruments and eversion methods of the present invention have many advantages. The present invention is less traumatic to the intima of the vessel during the eversion procedure than conventional surgical graspers and the like. The present invention is easy for the surgeon to use without assistance and requires only a few steps to operate. The present invention is useful for a wide range of blood vessel sizes, particularly small vessels, e.g., having a diameter of about 2–3 mm or less. In addition, the present invention is useful on one end of a vessel, when the opposite end is already attached to the patient (e.g., at the distal anastomosis of a patient undergoing a CABG procedure). The present invention also allows for the proper length of everted tissue over the tube, bushing, or the like, depending on the requirements of the anastomosis device or method being used. Finally, the present invention may be manufactured inexpensively.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

Although this invention has been shown and described with respect to detailed embodiments thereof, it will be understood by those skilled in the art that various changes in form and detail thereof may be made without departing from the spirit and scope of the claimed invention.

What is claimed is:

1. An instrument for evening an end of a vessel, comprising:
   a hollow frame having a distal end, a proximal end, and an axial bore, said axial bore having a distal section and a proximal section;
   a mandrel member mounted within the distal section of said axial bore, the mandrel having a proximal end and a distal end, the distal end partially extending from the distal end of the hollow frame, said mandrel member comprising a sheet of spring-like material rolled into a substantially conical shape, having a proximal end, a distal end, an inner surface and an inner lumen; and
   a plunger member slidably mounted in said axial bore and axially moveable therein, said plunger member having a distal end and a proximal end, said plunger moveable in the lumen of the mandrel member, said distal end of the plunger member engaging the inner surface of said mandrel member when said plunger is moved from a retracted position to an extended position, thereby causing the distal end of said mandrel member to expand radially outward and the proximal end of said mandrel member to contract radially inward.

2. The instrument of claim 1, comprising a biasing element mounted in the axial bore of the plunger member and engaging the plunger member to bias the plunger member to the retracted position.

3. The instrument of claim 2, wherein the biasing element comprises a spring disposed about the plunger and in engagement with the frame.

4. The instrument of claim 1 wherein the proximal end of the plunger extends out from the proximal end of the frame.

5. The instrument of claim 1, wherein the frame comprises a substantially circular cross-section.

6. The instrument of claim 1 wherein the frame comprises a substantially cylindrical configuration.

7. The instrument of claim 1, wherein the plunger comprises a substantially cylindrical configuration.

8. The instrument of claim 1 wherein the distal end of the plunger is blunt.

9. The instrument of claim 1 wherein the distal end of the plunger is curved.

10. A combination comprising:
   I. a tubular member comprising a distal end, a proximal end, an outer surface and an axial bore; and
   II. an instrument for everting an end of a vessel, comprising:
      a hollow frame having a distal end, a proximal end, and an axial bore, said axial bore having a distal section and a proximal section;
      a mandrel member mounted within the distal section of said axial bore, the mandrel having a proximal end and a distal end, the distal end partially extending from the distal end of the hollow frame, said mandrel member comprising a sheet of spring-like material rolled into a substantially conical shape, having a proximal end, a distal end, an inner surface, and an inner lumen; and a plunger member slidably mounted in said axial bore and axially moveable therein, said plunger member having a distal end and a proximal end, said plunger moveable in the lumen of the mandrel member, said distal end of the plunger member engaging the inner surface of said mandrel member when said plunger is moved from a retracted position to an extended position, thereby causing the distal end of said mandrel member to expand radially outward and the proximal end of said mandrel member to contract radially inward.

11. The combination of claim 10, comprising a biasing element mounted in the axial bore of the plunger member for engaging the plunger member to bias the plunger member to the retracted position.

12. The combination of claim 11, wherein the biasing element comprises a spring disposed about the plunger and in engagement with the frame.

13. The combination of claim 10, wherein the proximal end of the plunger extends out from the proximal end of the frame.

14. The combination of claim 10, wherein the frame comprises a substantially circular cross-section.

15. The combination of claim 10 wherein the frame comprises a substantially cylindrical configuration.

16. The combination of claim 10, wherein the plunger comprises a substantially cylindrical configuration.

17. The combination of claim 10 wherein the distal end of the plunger is blunt.

18. The combination of claim 10 wherein the distal end of the plunger is curved.

19. A method for everting the end of a vessel, comprising the steps of:

providing a tubular member, said tubular member comprising a distal end, a proximal end, an outer surface and an axial bore;

providing an instrument far everting an end of a vessel, comprising:

a hollow frame having a distal end, a proximal end, and an axial bore, said axial bore having a distal section and a proximal section;

a mandrel member mounted within the distal section of said axial bore, the mandrel having a proximal end and a distal end, the distal end partially extending from the distal end of the hollow frame, said mandrel member comprising a sheet of spring-like material rolled into a substantially conical shape, having a proximal end, a distal end, an inner surface, and an inner lumen; and a plunger member slidably mounted in said axial bore and axially moveable therein, said plunger member having a distal end and a proximal end, said plunger moveable in the lumen of the mandrel member, said distal end of the plunger member engaging the inner surface of said mandrel member when said plunger is moved from a retracted position to an extended position, thereby causing the distal end of said mandrel member to expand radially outward;

inserting a vessel into the tubular member such that a distal end section of the vessel extends out from the distal end of the tubular member;

inserting the distal end of the mandrel member into the lumen in the distal end of the vessel;

expanding the distal end of the mandrel member radially outward by moving the plunger from the refracted position to the extended position, thereby expanding radially the distal end of the vessel;

everting the vessel portion over the distal end of the tubular member by moving the expanded distal end of the mandrel member and the expanded distal end of the vessel over the outer surface of the tubular member; and withdrawing the mandrel member from the vessel and tubular member.

20. The method of claim 19, wherein the proximal end of the mandrel member of the instrument contracts radially inward when the plunger is moved from the retracted to the extended position.

* * * * *